United States Patent [19]

Hu

[11] Patent Number: 6,014,419

[45] Date of Patent: Jan. 11, 2000

[54] CT CONE BEAM SCANNER WITH FAST AND COMPLETE DATA ACQUISTION AND ACCURATE AND EFFICIENT REGIONAL RECONSTRUCTION

[76] Inventor: Hui Hu, 1030 Ridge Rd., Waukesha, Wis. 53186

[21] Appl. No.: 08/966,155

[22] Filed: Nov. 7, 1997

[51] Int. Cl.[7] ........................................................ A61B 6/03
[52] U.S. Cl. .................................................. 378/4; 378/901
[58] Field of Search .................................. 378/4, 15, 901

[56] References Cited

U.S. PATENT DOCUMENTS

| | | | |
|---|---|---|---|
| 5,170,439 | 12/1992 | Zeng et al. | 382/6 |
| 5,663,995 | 9/1997 | Hu | 378/15 |
| 5,706,325 | 1/1998 | Hu | 378/4 |
| 5,784,481 | 7/1998 | Hu | 382/131 |
| 5,926,521 | 7/1999 | Tam | 378/4 |

*Primary Examiner*—David Vernon Bruce

*Attorney, Agent, or Firm*—Skarsten Law Offices S.C.

[57] ABSTRACT

A method is provided for reconstructing an image of an object, for use in an imaging system wherein a detector is mounted for measuring radiation emanating in a cone beam of rays which converge at a focal point. The method includes the step of establishing relative movement between the cone beam focal point and the object along a composite scan path, comprising primary and supplementary scan path components, the supplementary path usefully comprising a linear or helical path. The method further includes acquiring a set of cone beam data of the object with the detector during movement along the supplementary scan path component, computing a set of values of an intermediate function from the cone beam data, each of said computed values having an associated location defined by a prespecified point grid lying on the detector plane, and employing each of the computed values in a back-projection operation to determine the value of a reconstruction function, for use in forming an image of the object. The method also includes a strategy of imaging longitudinally-unbounded object section by section

27 Claims, 6 Drawing Sheets

CT CONE BEAM SCANNER WITH FAST AND COMPLETE DATA ACQUISTION AND ACCURATE AND EFFICIENT REGIONAL RECONSTRUCTION

BACKGROUND OF THE INVENTION

The present invention generally pertains to cone beam computed tomography (CT) imaging apparatus and method. More particularly, the invention pertains to such apparatus and method that acquires and processes cone beam projection data acquired along a trajectory comprising a circular or other primary scan path (i.e., orbit) supplemented by a helical or other supplementary scan path.

Cone beam CT imaging has developed as an important technique in constructing a three-dimensional CT image. According to such technique, an X-ray source irradiates the object with conical shaped X-rays while traversing a prescribed scan path or trajectory, to project an image of the object, in the form of cone beam X-ray data, onto an array of two-dimensional detector elements. The detector elements acquire or receive the projected cone beam data, which is then processed to provide the reconstructed image of the object.

Scan path is an essential consideration in cone beam imaging. Different scan paths represent different data measurement procedures and call for different data processing algorithms (reconstruction algorithms) to produce the reconstructed images. Developing accurate, efficient and robust reconstruction algorithms for the scan paths of practical interest has been the focus of many research groups. As a prerequisite for high fidelity (exact) reconstruction, the scan path employed should provide sufficient cone beam data measurements.

The reconstruction algorithm for generating a primary part of the reconstructed function from circular path cone beam CT was given by Feldkamp et al, "Practical Cone-beam Algorithm", J. Opt. Soc. Am., pp. 612–619 (1984). The algorithm for generating the entire portion of the reconstructed function that can be derived from circular path cone beam CT was recently given by U.S. Pat. No. 5,400,255, issued Mar. 21, 1995, to Hui Hu, the inventor herein. However, it is well known that the circular scan path is likely to provide insufficient cone beam data and may generate erroneous results.

Various scanning geometries (paths) have been developed to ensure that sufficient data is acquired. In one such geometry, the scan path comprises a circular path in combination with a linear path, which is orthogonal to the plane containing the circular path. Various algorithms are currently available for use in processing cone beam data acquired by scanning along a combined circle-and-line path and constructing an image therefrom. However, some of such algorithms, such as set forth in an article by H. Kudo and T. Saito, entitled, "Derivation and implementation of a cone-beam reconstruction algorithm for non-planar orbits", IEEE Trans. Med. Imag. vol. 13 pp. 196–211 (1994) require excessive data processing resources. Other of such algorithms, such as set forth in an article by G Zheng and G. Gullberg entitled, "A cone beam tomography algorithm for orthogonal circle-and-line orbit", Phys. Med. Biol., vol. 37(4) pp. 563–577 (1992) and in U.S. Pat. No. 5,170,439 have been found to be inaccurate.

More recently, an reconstruction algorithm has been developed by the inventor for generating, from the linear scanned data, a portion of the reconstructed function supplementary to the primary portion derivable from the circular scan. Thus, this supplementary portion is then additively combined with the primary portion which is derived from the circular scan in accordance to U.S. Pat. No. 5,400,255 to provide a complete reconstruction of the function of the object. While this technique has provided significant benefits in terms of the reconstruction accuracy, it has been found that a substantial amount of processing effort is still required, in order to derive the linear scan portion of the reconstructed function. It would be desirable to significantly reduce the data processing load by improving the efficiency of the technique.

The circle-and-line scan path is of great practical interest, since it can be readily implemented by rotating the scanner or the object around a circle in the circular scan and by translating the object along the axis of rotation in the linear scan. However, since no rotation is allowed during the linear scan, the time it takes to completely stop the rotation before the linear scan and to reestablish the rotation for the sequential circular scan after the linear scan is too long for some applications, especially when using the circle-and-line scan repeatedly. To eliminate he lengthy switching time and therefore increase the overall data acquisition speed, the present invention proposes a new scan path, i.e., the circle-and-helix scan path. It would be desirable to develop a reconstruction algorithm for this scan path.

For most applications in medicine and some applications in industry, the longitudinal extent of the object to be imaged exceeds the length which can be scanned by the scanner in one scan. Such an object is referred to as a longitudinally-unbounded object. One practical consideration in cone beam CT system development is how to image the longitudinally-unbounded object when only a portion of it is of interest or can be imaged in one scan due to the limited detector extent. Most of the methods developed cannot meet this challenge. It would be desirable to be able to develop a strategy for exact reconstruction of the longitudinally-unbounded object through a series of regional scans and reconstructions.

SUMMARY OF THE INVENTION

In a CT imaging system comprising a source of cone beam radiation and a two-dimensional array of detector elements which are selectively positioned with respect to an object, a new and improved cone beam scan and reconstruction technique is provided.

The technique includes the step of establishing relative movement between the cone beam focal point and the object along a composite scan path comprising a circular orbit or other trajectory which lies in a single plane, supplemented by a linear, helical or other scan path which is not confined to the plane. These two scan path components are called the primary orbit and the supplementary orbit respectively. The cone beam source irradiates the object during such movement to project cone beam data onto the two-dimensional detector, the projected data comprising a primary data set and a supplementary data set acquired from the primary and supplementary orbits, respectively. Two important embodiments, i.e., the circle-and-line and circle-and-helix scan path, are explicitly discussed hereinafter.

The technique includes new cone beam CT reconstruction algorithms. These reconstruction algorithms are based on the idea of decomposing the function to be reconstructed into two components: 1) the primary component, which can be derived from the primary orbit; and 2) the supplementary component, which is the remaining part of the function to be reconstructed. The algorithms propose to compute the primary and supplementary components of the reconstructed function respectively from the primary and supplementary cone-beam data.

The technique also includes a new method of computing the supplementary component of the reconstructed function from the supplementary data set. The method comprises 1) computing the values of an intermediate function on a set of points on a detector plane; and 2) back-projecting the intermediate function to produce the supplementary component of the reconstruction. This technique further includes adopting a special sparse grid on which the intermediate function is computed, and/or adopting a special sparse three-dimensional grid on which a part of the reconstructed function is initially computed.

The technique further includes a strategy for imaging a longitudinally-unbounded object. The method comprises 1) identifying a region for each scan where an error-free reconstruction can be obtained, and 2) combining multiple error-free reconstructions from multiple scans to generate an exact reconstruction of the longitudinally-unbounded object over the entire region-of-interest.

OBJECTS OF THE INVENTION

An object of the invention is to provide a cone beam CT method and apparatus for high speed acquisition of a cone beam projection data set that is sufficient for an exact reconstruction.

Another object is to improve accuracy (i.e., fidelity) and efficiency (i.e., speed) in generating the reconstruction of an object.

Another object is to extend the usefulness and robustness of a cone beam CT system of the above type to image a longitudinally-unbounded object.

These and other objects of the invention will become more readily apparent from the ensuing specification, taken together with the accompanying drawings.

DETAILED DESCRIPTION OF THE PREFERRED EMBODIMENT

Figure 1:
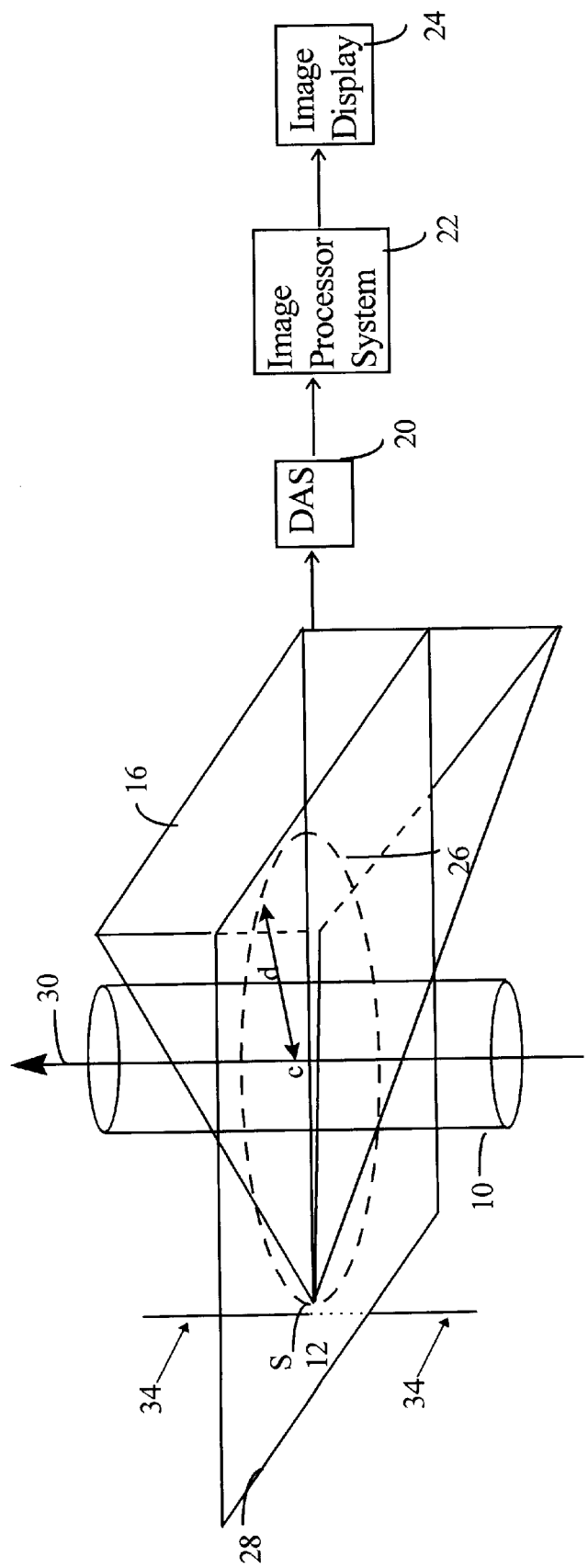
FIG. 1 is a schematic diagram illustrating principal elements of a CT cone beam imaging system and a circle-and-line scan path.

Referring to FIG. 1, there are shown the principal components of a cone-beam CT imaging system. A cone beam source 12 is positioned to irradiate the object to be imaged 10, and to thereby project a conical shaped beam onto a two-dimensional detector array 16, comprising a matrix array of discrete detector elements (not shown in detail). The cone-beam projection measurements represent, in analog form, the number of photons that penetrate the object along the lines connecting the cone beam focal point 12 and the respective detector elements. Such data is coupled to a Data Acquisition System (DAS) 20, which converts analog data from the respective detector elements into digital form for subsequent processing. The digitized projection data is coupled to an image reconstruction processor system 22, which operates on the projection data to reconstruct an image representation of the object 10. The reconstructed images may be presented in viewable form, for example, by means of an image display 24.

FIG. 1 further shows a circular orbit of motion 26 for the cone beam source 12 around the object 10, such orbit lying in a single plane called the mid-plane 28. In one arrangement, detector array 16 is constrained to move with source 12, while object 10 remains still therebetween. Cone-beam projection data is acquired by detector array 16 for successive positions of the cone beam source 12 as the source 12 traverses the circular orbit 26. A z-axis 30 represents the axis of rotation, which passes through the center of the circle, the point C, in orthogonal relationship with mid-plane 28.

FIG. 1 further shows that the cone beam focal point 12 can be moved along a linear orbit 34, which is not confined to the mid-plane.

Figure 3:
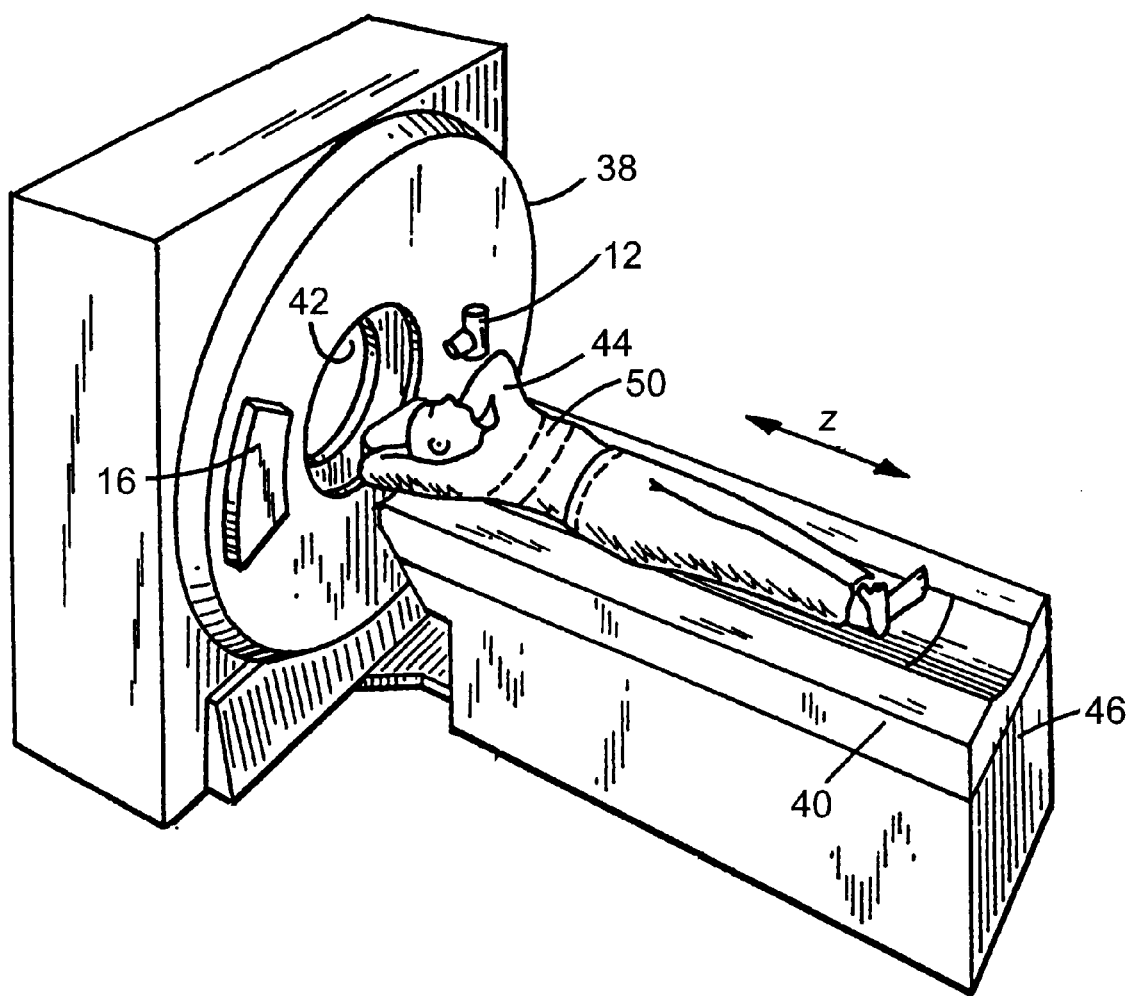
FIG. 3 is a perspective view further illustrating a conventional CT imaging system for use in implementing some embodiments of the invention.

The circle-and-line scan path can be readily implemented by a conventional CT system. Referring to FIG. 3, there is shown a conventional CT system substantially comprising a gantry 38 and a table 40. The table 40, which is slideable upon base 46, moves a patient 44 linearly, along the z-axis. Thus, table 40 can be operated to position a selected section 50 of the patient within the bore 42, so that images can be taken therethrough.

Referring further to FIGS. 3 and 1 together, there is shown the source 12 and detector array 16 mounted on rotatable gantry 38, on opposing sides of the bore 42. Accordingly, the circular orbit 26 may be established by rotation of gantry 38. The linear orbit 34 may be established by linear movement of the patient table 40, while source 12 and detector array 16 remain stationary.

The circle-and-line orbit is one embodiment of the present invention. However, for the circle-and-line orbit, no rotation is allowed during the linear scan. Thus, it is necessary to stop the gantry rotation after the circular scan in order to start the linear scan, and to reestablish the gantry rotation after the linear scan in order to start the next circular scan. For some applications, the time spent on switching between the circular and linear scans could represent a very significant portion of the overall data acquisition time, especially when switching back and forth repeatedly in multiple scans.

Figure 2:
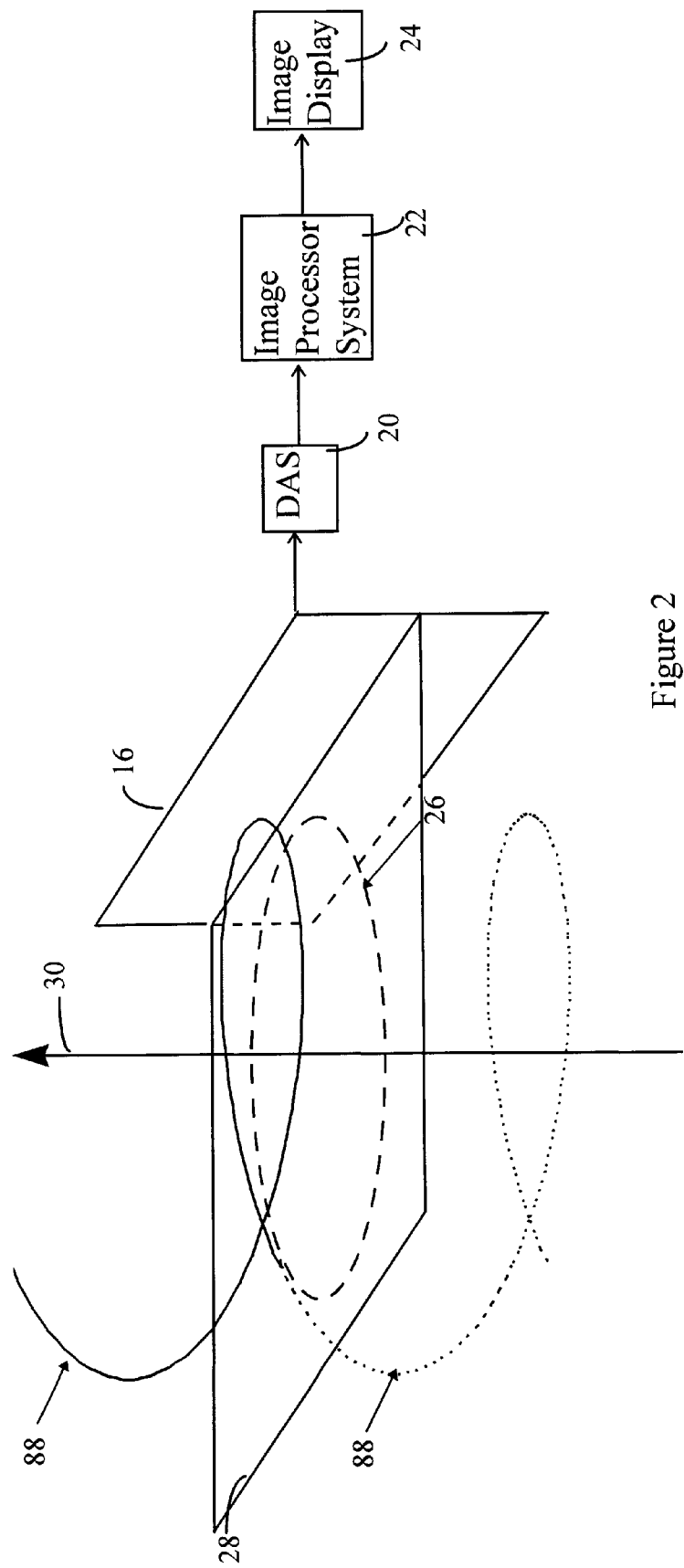
FIG. 2 is a schematic diagram illustrating principal elements of a CT cone beam imaging system and a circle-and-helix scan path.

As another embodiment of the present invention, a new scan orbit comprising a circle 26 and a helix 88 is proposed and shown in FIG. 2. The circle-and-helix scan orbit can also be readily implemented by a conventional CT system by a relative rotational movement and a relative linear movement between the object and the gantry, as described above in connection with FIG. 3. Since the rotational movement is required in both circular and helical scans, the lengthy switching time required for stopping and reestablishing the rotational movement is eliminated. This represents a significant improvement in the overall data acquisition speed.

The circle-and-line scan path and circle-and-helix scan path represent two examples of a class of general composite scan paths. Each composite scan path in this class comprises a primary orbit lying in a single plane 28 and a supplementary orbit not confined to the plane 28 containing the primary orbit. The plane containing the primary orbit is referred to as the mid-plane. It is to be understood that the primary orbit, besides the circular orbit discussed herein, also includes an elliptical or other form in other embodiments, provided that such orbit lies entirely in a single plane. Similarly, the supplementary orbit, besides the linear or helical scan orbit discussed herein, also includes other scan paths not confined to the mid-plane.

The cone-beam projection data sets acquired from the primary and supplementary scan orbits are referred to respectively as the primary and supplementary data sets. More particularly, the cone-beam projection data sets acquired from the circular, linear and helical scan orbits are referred to respectively as the circularly, linearly and helically scanned data sets.

As another embodiment of the present invention, new cone beam CT reconstruction algorithms are proposed for the primary-and-supplementary orbit in general, and for the circle-and-line scan path and circle-and-helix scan path in particular. These reconstruction algorithms are based on the idea of decomposing the function to be reconstructed into two components: 1) the primary component, which can be derived from the primary orbit; and 2) the supplementary component, which is the remaining part of the function to be reconstructed. The algorithms propose to compute the primary and supplementary components of the reconstructed function respectively from the primary and supplementary data sets.

Figure 4:
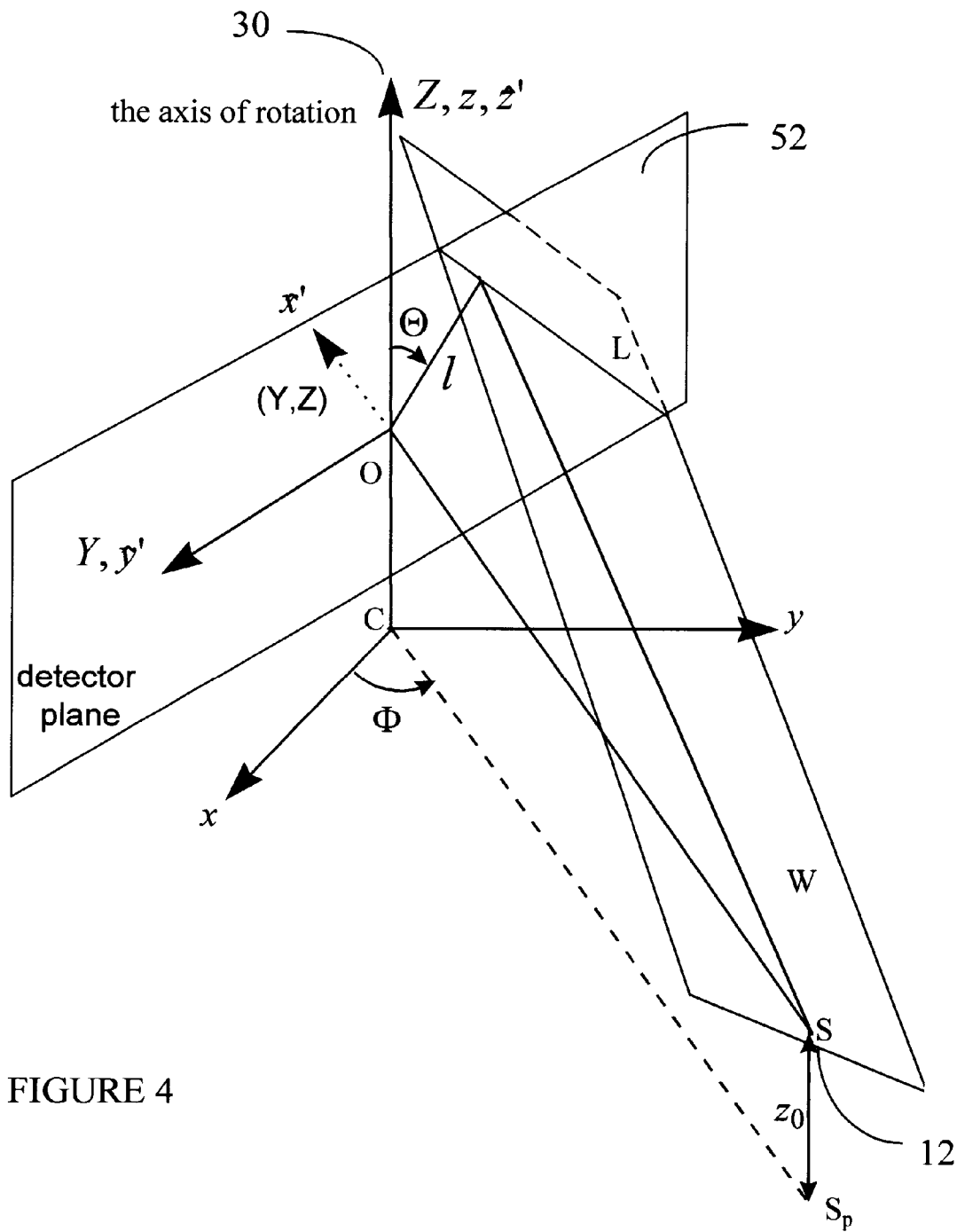
FIG. 4 is a view showing a cone beam imaging arrangement with associated coordinate systems and spatial parameters imposed thereon for use in further illustrating some embodiments of the invention.

FIG. 4 illustrates the physical meanings of some elements and parameters used in the presented invention. The x, y, and z axes in FIG. 4 represent a Cartesian coordinate system that is fixed relative to the object to be imaged. The z axis is along the axis of rotation 30 and the x and y axes lie in the mid-plane 28. The point C is the origin of this fixed coordinate system. The position of a point is expressed as $\vec{r}$ or (x, y, z) in this Cartesian coordinate system. In FIG. 4, the point S represents the focal point of a cone beam projection. The point O is the perpendicular projection point of the point S onto the axis of rotation 30. Since cone beam source 12 both rotates and translates, it is useful to provide an additional coordinate system that moves with the cone beam source. The orthogonal vectors of this moving coordinate system are $(\hat{x}', \hat{y}', \hat{z}')$, where $\hat{x}'$ and $\hat{z}'$ are directed along the line SO and the axis of rotation 30, i.e., the z-axis, respectively. The point O is the origin of this moving coordinate system. The rotation movement of the cone beam source is characterized by its rotational angle, $\phi$, relative to the fixed coordinate system. The translational movement of the cone beam source is characterized by its z elevation, $z_0$, relative to the mid-plane 28. The distance from O to S is denoted as d.

A special plane, referred to as the detector plane, is defined as a plane perpendicular to the line SO. Without losing generality, the detector plane 52 discussed herein and shown in FIG. 4 is chosen to contain the z-axis. Any physical detector arrangement can be converted to this detector plane by means of a mapping process. Thus, the position on the detector plane, identified by the coordinates (Y,Z), also corresponds to the physical position of the detector element. Therefore, a set of cone beam projections acquired from the primary and supplementary scan orbit can be characterized as $\hat{P}_\phi(Y,Z)$ and $\hat{P}_{z0}(Y,Z)$ respectively, where the position of the cone beam source on the primary orbit is characterized by its rotational angle $\phi$, while the position of the cone beam source on the supplementary orbit is characterized by its distance $z_0$ to the mid-plane. It will be readily apparent that $z_0$ will have a non-zero value only when cone beam source 12 is positioned along the supplementary orbit above or below the mid-plane 28.

Both the primary and supplementary cone beam data sets are weighted as follows to generate weighted projection data:

$$P_{\phi \text{ or } z0}(Y, Z) = \frac{d}{\sqrt{d^2 + Y^2 + Z^2}} \hat{P}_{\phi \text{ or } z0}(Y, Z) \tag{1}$$

U.S. Pat. No. 5,400,255, issued Mar. 21, 1995 to Hui Hu, the inventor herein, teaches that for the circle orbit, any function to be reconstructed $f(\vec{r})$ can be decomposed into the following three terms:

$$f(\vec{r}) = f_{C_0}(\vec{r}) + f_{C_1}(\vec{r}) + f_L(\vec{r}) \tag{2}$$

The $f_{C_0}(\vec{r})$ term, computed from the circularly scanned data set, corresponds to the Feldkamp reconstruction, which is formulated as the following two steps:

$$1)\ p_\phi(Y,Z) = \int dY' P_\phi(Y',Z) h(Y-Y') \tag{3a}$$

$$2)\ f_{C_0}(\vec{r}) = \frac{1}{4\pi^2} \oint d\phi \frac{d^2}{(d + \vec{r} \cdot \hat{x}')^2} p_\phi(Y_0, Z_0)_{Y_0 = \frac{d\vec{r}\cdot\hat{y}'}{d+\vec{r}\cdot\hat{x}'}, Z_0 = \frac{dz}{d+\vec{r}\cdot\hat{x}'}} \tag{3b}$$

where, h(Y) is the kernel of the ramp filter.

U.S. Pat. No. 5,400,255 teaches how to compute $f_{C_1}(\vec{r})$ from the circular scan. It can be summarized as the following two steps:

$$1)\ q_\phi(Z) = \frac{\partial}{\partial Z} \int dY P_\phi(Y, Z) \tag{4a}$$

$$2)\ f_{C_1}(\vec{r}) = -\frac{1}{4\pi^2} \oint d\phi \frac{z}{(d + \vec{r}\cdot\hat{x}')} q_\phi(Z_0)_{Z_0 = \frac{dz}{d+\vec{r}\cdot\hat{x}'}} \tag{4b}$$

In accordance with the present invention, the $f_{C_0}(\vec{r})$ and $f_{C_1}(\vec{r})$ terms combined form the primary component of the function to be reconstructed. The $f_L(\vec{r})$ term represents the supplementary component of the function to be reconstructed. As will be discussed hereinafter, decomposing the function to be reconstructed into several terms (such as shown in Equation 2) enables development of a term-specific technique to further improve the accuracy and efficiency of reconstruction of each term and therefore of the overall reconstruction.

U.S. Pat. No. 5,400,255 proposes to estimate $f_L(\vec{r})$ when only the circularly scanned data is available. A related technique, described hereinafter, teaches how to accurately generating $f_L(\vec{r})$ from the linearly scanned data set. Such technique can be summarized as the following three steps:
1) A line integral, $\Sigma_{z_0}(l,\downarrow)$, may be computed by summing the weighted projected data $P_{z0}(Y,Z)$ at each (Y,Z) position along the line L as follows:

$$\Sigma_{z_0}(l,\downarrow) = \int\int dY dZ P_{z_0}(Y,Z) \delta(Y \sin\downarrow + Z \cos\downarrow - l) \tag{5a}$$

Referring to FIG. 4, the line L represents the intersection line between a plane W containing the source (i.e., the focal point) S 12 and the detector plane 52. The line L is characterized by coordinates $(l,\downarrow)$, where $l$ is the distance from the origin O to the line, and $\downarrow$ is the angle the normal of the line L makes with the z-axis 30.

For each cone beam source position $z_0$ along the linear scan orbit, computation of the line integration, $\Sigma_{z_0}(l,\downarrow)$, is carried out only for those lines which correspond to those planes W intersecting the object but not intersecting the circular scan orbit. These lines can be characterized by the following equation:

$$2lz_0 \cos\downarrow + z_0^2 \cos^2\downarrow - d^2 \sin^2\downarrow > 0 \quad (5b)$$

To reflect this selective computation, the following selecting function $w_{z_0}(l,\downarrow)$ is introduced:

$$w_{z_0}(l,\Theta) = \begin{cases} 1 & \text{when } 2lz_0\cos\Theta + z_0^2\cos^2\Theta - d^2\sin^2\Theta > 0 \\ 0 & \text{otherwise} \end{cases} \quad (5c)$$

2) An intermediate function, $H_{z_0}(l,\downarrow)$, is computed based on the line integrals $\Sigma_{z_0}(l,\downarrow)$ and the selecting function $w_{z_0}(l,\downarrow)$ as follows:

$$H_{z_0}(l,\Theta) = |\cos\Theta| w_{z_0}(l,\Theta) \left( \frac{d^2+l^2}{d^2} \frac{\partial^2 \Sigma_{z_0}(l,\Theta)}{\partial^2 l} + \frac{2l}{d^2} \frac{\partial \Sigma_{z_0}(l,\Theta)}{\partial l} \right) \quad (5d)$$

3) The linear component, $f_L(\vec{r})$, could be determined by integrating $H_{z_0}(l,\downarrow)$ over $z_0$ and $\downarrow$ as follows:

$$f_L(\vec{r}) = -\frac{1}{4\pi^2(d+\vec{r}\cdot\hat{x}')} \int dz_0 \int_0^\pi d\Theta\, H_{z_0}(l,\Theta)\Big|_{l=\frac{d\vec{r}\cdot\hat{y}'}{d+\vec{r}\cdot\hat{x}'}\sin\Theta+\frac{d(z-z_0)}{d+\vec{r}\cdot\hat{x}'}\cos\Theta} \quad (5e)$$

Though computing $f_L(\vec{r})$ using Equations 5 significantly improves the reconstruction accuracy, it still requires a substantial amount of processing effort. This is because the integral operation $\int_0^\pi d\downarrow H_{z_0}(l,\downarrow)$ must be carried out in the backprojection step (Equation 5e) for all the reconstruction points, $\vec{r}$ or $(x,y,z)$, and for each $z_0$ along the linear scan, which is very time-consuming.

In accordance with the present invention, the second and third steps of the previous invention are modified as follows:
2) A new intermediate function, $B_{z_0}(Y,Z)$, is computed based on the line integrals $\Sigma_{z_0}(l,\downarrow)$ and the selecting function $w_{z_0}(l,\downarrow)$ as follows:

$$B_{z_0}(Y,Z) = \int_0^\pi d\Theta\, H_{z_0}(l,\Theta)\Big|_{l=Y\sin\Theta+Z\cos\Theta} \quad (6d)$$

$$= \int_0^\pi d\Theta |\cos\Theta| w_{z_0}(l,\Theta)\left(\frac{d^2+l^2}{d^2}\frac{\partial^2 \Sigma_{z_0}(l,\Theta)}{\partial^2 l} + \frac{2l}{d^2}\frac{\partial \Sigma_{z_0}(l,\Theta)}{\partial l}\right)_{l=Y\sin\Theta+Z\cos\Theta}$$

3) The linear component, $f_L(\vec{r})$, is determined by back-projecting $B_{z_0}(Y,Z)$ as follows:

$$f_L(\vec{r}) = -\frac{1}{4\pi^2(d+\vec{r}\cdot\hat{x}')} \int dz_0 B_{z_0}(Y_0,Z_0)\Big|_{Y_0=\frac{d\vec{r}\cdot\hat{y}'}{d+\vec{r}\cdot\hat{x}'},Z_0=\frac{d(z-z_0)}{d+\vec{r}\cdot\hat{x}'}} \quad (6e)$$

In this new formulation, the new intermediate function $B_{z_0}(Y,Z)$, representing the integral $\int_0^\pi d\downarrow H_{z_0}(l,\downarrow)$, is pre-calculated on a set of points $(Y,Z)$ on the detector plane. This calculation is carried out once for each $z_0$ along the linear scan prior to the backprojection step. In the backprojection step of Equation 6e, the value of the intermediate function $B_{z_0}(Y,Z)$ at any point, $(Y_0,Z_0)$, is computed by interpolation of those values pre-calculated on the grid $(Y,Z)$, instead of evaluating $$\int_0^\pi d\Theta\, H_{z_0}(l,\Theta)$$

repeatedly as suggested by Equation 5e. The grid $(Y,Z)$ on which the intermediate function $B_{z_0}(Y,Z)$ is pre-calculated is referred to as the pre-calculation grid.

The new formulation takes the integral $$\int_0^\pi d\Theta\, H_{z_0}(l,\Theta)$$

out of the computationally intensive backprojection operation, which loops through all the reconstruction points, $\vec{r}$ or $(x,y,z)$. As a result, the processing efficiency is significantly improved.

As an important embodiment of the present invention, the reconstruction algorithm for the circle-and-helix scan orbit shown in FIG. 2 is proposed in a similar form as follows: 1) compute the $f_{C_0}(\vec{r})$ and $f_{C_1}(\vec{r})$ reconstruction using Equations 3 and 4 respectively; 2) compute the supplementary component, $f_L(\vec{r})$, from the helically scanned data using the following formulae (Equations 7a, below); and 3) combine the three terms to form a complete reconstruction $f(\vec{r})$.

Similar to the reconstruction from the linear scan, the reconstruction of the supplementary component, $f_L(\vec{r})$, from the helically scanned data also consists of three steps:
1) A line integral, $\Sigma_{z_0}(l,\downarrow)$, may be computed by summing the weighted projected data $P_{z_0}(Y,Z)$ at each $(Y,Z)$ position along the line L as follows:

$$\Sigma_{z_0}(l,\downarrow) = \int\int dY dZ P_{z_0}(Y,Z)\delta(Y\sin\Theta + Z\cos\downarrow - l) \quad (7a)$$

where the selecting function $w_{z_0}(l,\downarrow)$ is defined as:

$$w_{z_0}(l,\Theta) = \begin{cases} 1 & \text{when } 2lz_0\cos\Theta + z_0^2\cos^2\Theta - d^2\sin^2\Theta > 0 \\ 0 & \text{otherwise} \end{cases} \quad (7c)$$

2) A new intermediate function, $B_{z_0}(Y,Z)$, is computed based on the line integrals $\Sigma_{z_0}(l,\downarrow)$ and the selecting function $w_{z_0}(l,\downarrow)$ as follows:

$B_{z_0}(Y,Z)=$ $$B_{z_0}(Y,Z) = \int_0^\pi d\Theta \left|\sin\Theta - \frac{k}{d}\cos\Theta\right| w_{z_0}(l,\Theta)\left(\frac{d^2+l^2}{d^2}\frac{\partial^2 \Sigma_{z_0}(l,\Theta)}{\partial^2 l} + \frac{2l}{d^2}\frac{\partial \Sigma_{z_0}(l,\Theta)}{\partial l}\right)_{l=Y\sin\Theta+Z\cos\Theta} \quad (7d)$$

3) The linear component, $f_L(\vec{r})$, is determined by backprojecting $B_{z_0}(Y,Z)$ as follows:

$$f'_L(\vec{r}) = -\frac{1}{4\pi^2(d+\vec{r}\cdot\hat{x}')}\frac{d}{k}\int dz_0 B_{z_0}(Y_o, Z_o)_{Y_o=\frac{d\vec{r}\cdot\hat{y}'}{d+\vec{r}\cdot\hat{x}'}, Z_o=\frac{d(z-z_0)}{d+\vec{r}\cdot\hat{x}'}} \quad (7e)$$

In Equations 7, $P_{z_0}(Y,Z)$ represents the weighted cone beam projection acquired from a helical scan, and k is a proportion factor so that $z_0=k\phi$.

The cone beam reconstruction algorithms for the circle-and-line or circle-and-helix orbit are explicitly given in Equations 1–7. It is to be understood that the reconstruction algorithms for other primary orbits, such as the elliptical orbit, and/or for other supplementary orbits can be derived by the coordinate transform method. Conventional examples of using such method are set forth in the following references: B. Horn, "Fan-beam reconstruction method," in Proc. IEEE, vol. 67, pp. 1616–1623 (1979); G. Gullberg and G. Zeng, "A cone-beam filtered backprojection reconstruction algorithm for cardiac single photon emission computed tomography," IEEE Trans. Med. Imag., vol. 11, no. 1, pp. 91–101 (1992); G. Wang, T. Lin, and P. Cheng, "A derivation-free noncircular fan-beam reconstruction formula", IEEE Trans. image processing, vol. 2, no. 4, pp. 543–547 (1992).

In a modification of the present invention, which further significantly improves the computational efficiency, it has been recognized that the supplementary component, $f_L(\vec{r})$, while changing rapidly along the z direction, varies slowly in the x and y directions.

Without utilizing this property of the $f_L(\vec{r})$ component, it would be assumed that the pre-calculation grid would be similar to the matrix of the detector elements projected on the detector plane. However, because of the property of the $f_L(\vec{r})$ component, a much sparser sampling of $B_{z_0}(Y,Z)$ along the Y direction should be sufficient. Thus, one can use a pre-calculation grid distinctly different from the matrix of the detector elements projected on the detector plane. More specifically, in the Y direction, the sampling spacing of the pre-calculation grid can be substantially greater (e.g., 10 times greater) than that of the detector elements projected on the detector plane without losing any information. On the other hand, in the Z direction, the sampling spacing of the pre-calculation grid is comparable to or slightly higher than that of the detector elements projected on the detector plane to maintain the high frequency content in the z direction. Increasing the Y sampling spacing by a factor of N will reduce the time for computing Equation 6d or 7d by roughly a factor of N. The factor for optimized image x-y pitch may be on the order of 10.

Applying a similar idea to the backprojection, the $f_L(\vec{r})$ in Equation 5e, 6e, or 7e can first be computed on a sparser three-dimensional point grid in image space, which, compared with full-size image grid, has a larger spacing between points in both the x and y directions. (Image space has rectilinear coordinates (x,y,z), where the z axis coincides with the Z-axis of the detector plane.) After the backprojection and before $f(\vec{r})$ is formed by combining three terms as described above, the values of $f_L(\vec{r})$ on a full-size image grid can be computed by interpolation of those on the sparser image grid. This sparser 3-D reconstruction is referred to as a thumbnail reconstruction of the full size reconstruction. Increasing the x-y pitch by a factor of N will reduce the computation time for Equation 5e, 6e, or 7e by roughly a factor of $N^2$. The factor N for optimized image x-y pitch may be on the order of 2–4.

It is to be noted that the two sparse sampling approaches mentioned above are general and can be used to improve the reconstruction efficiency of any function which has high frequency contents in one direction and low frequency contents in other directions. For example, the approach directed to sparse sampling in image space can be used to improve the computation efficiency of $f_{C1}(\vec{r})$ reconstruction (Equation 4b).

In a modification of the present invention, the concept of filtration can be used to improve reconstruction accuracy and stability. The filter can be applied to all or some of the components of the said reconstruction (Equation 2), prior to or after the backprojection step. The filter can be either shift-invariant or shift-variant, along one or multiple directions. More specifically, the filter along the z direction may be necessary.

Figure 5:
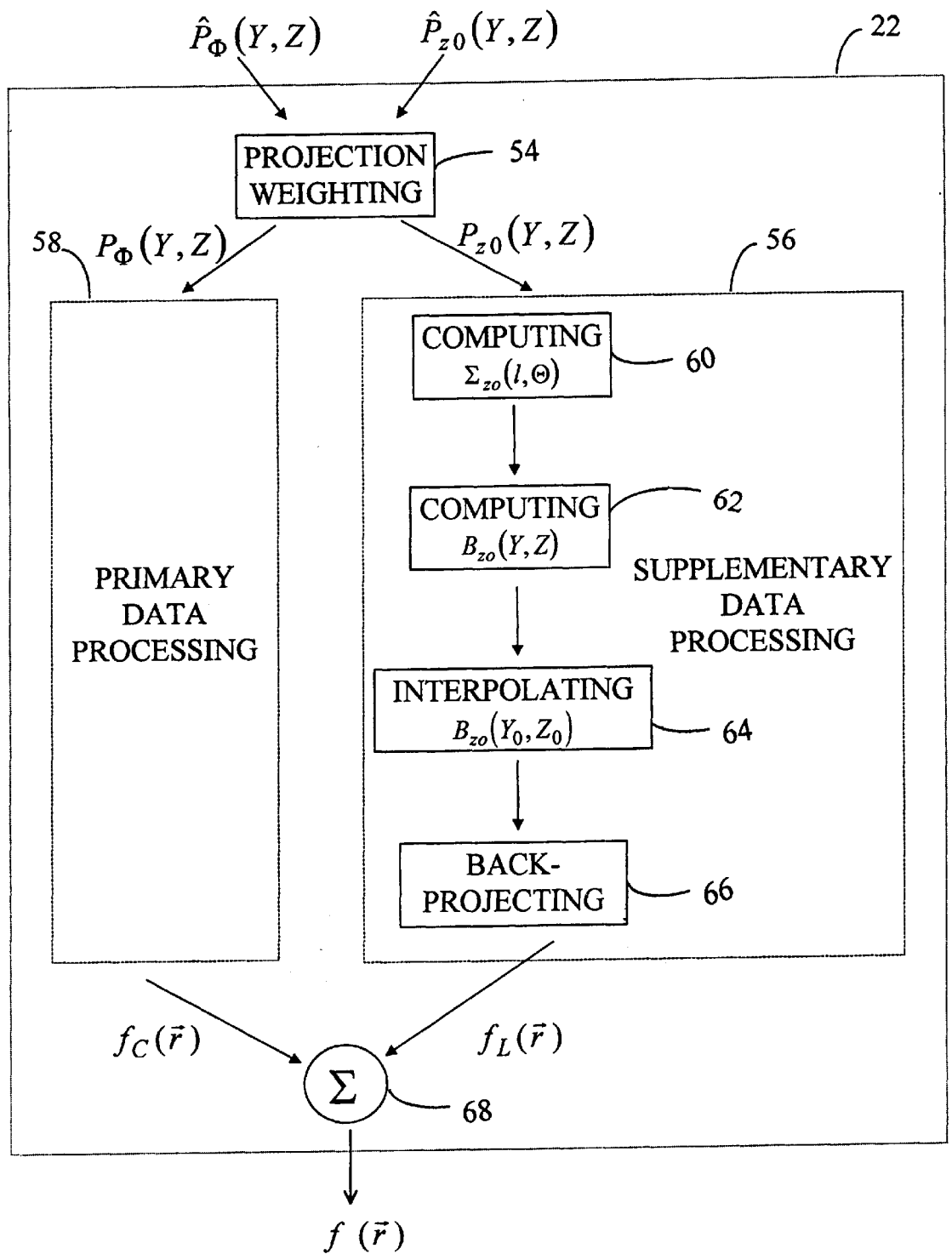
FIG. 5 is a block diagram demonstrating an implementation of some embodiments of the invention.

Referring to FIG. 5, there are shown certain operations performed in image processing system 22, in accordance with the above equations. Supplementary data $\hat{P}_{z_0}(Y,Z)$ and primary data $\hat{P}_\phi(Y,Z)$ are coupled to a weighting process block 54 in accordance with Equation 1.

The supplementary data is then processed separately in block 56. Referring further to FIG. 5, there is shown block 56 including a computation block 60, which operates to provide line integrals $\Sigma_{z_0}(l,\downarrow)$ by summing the weighted projection data $P_{z_0}(Y,Z)$ in accordance with Equation 5a or 7a above. Only the integrals along those line which correspond to planes not intersecting the primary orbit are computed. These lines are selected so that its spatial parameters $(Z_0,\downarrow,l)$ makes the selection function $w_{z_0}(l,\downarrow)$ non-zero, in accordance with Equation 5c or 7c. In block 62, the an intermediate function $B_{z_0}(Y,Z)$ from the line integrals is computed in accordance with Equation 6d or 7d. The in intermediate function is then interpolated and backprojected in blocks 64 and 66 to provide $f_L(\vec{r})$, in accordance with Equation 6e or 7e.

FIG. 5 further shows that the primary data $P_\phi(Y,Z)$ is sent to primary data process block 58, which computes image reconstruction functions $f_{c1}(\vec{r})$ and $f_{c0}(\vec{r})$ therefrom to provide the function $f_c(\vec{r})$.

The functions $f_L(\vec{r})$ and $f_c(\vec{r})$ are respectively coupled to a summing device 68 to provide the function $f(\vec{r})$. It will be understood that certain conventional functions performed by processor 22 are not necessary for understanding the invention, and are accordingly not shown.

Figure 6:
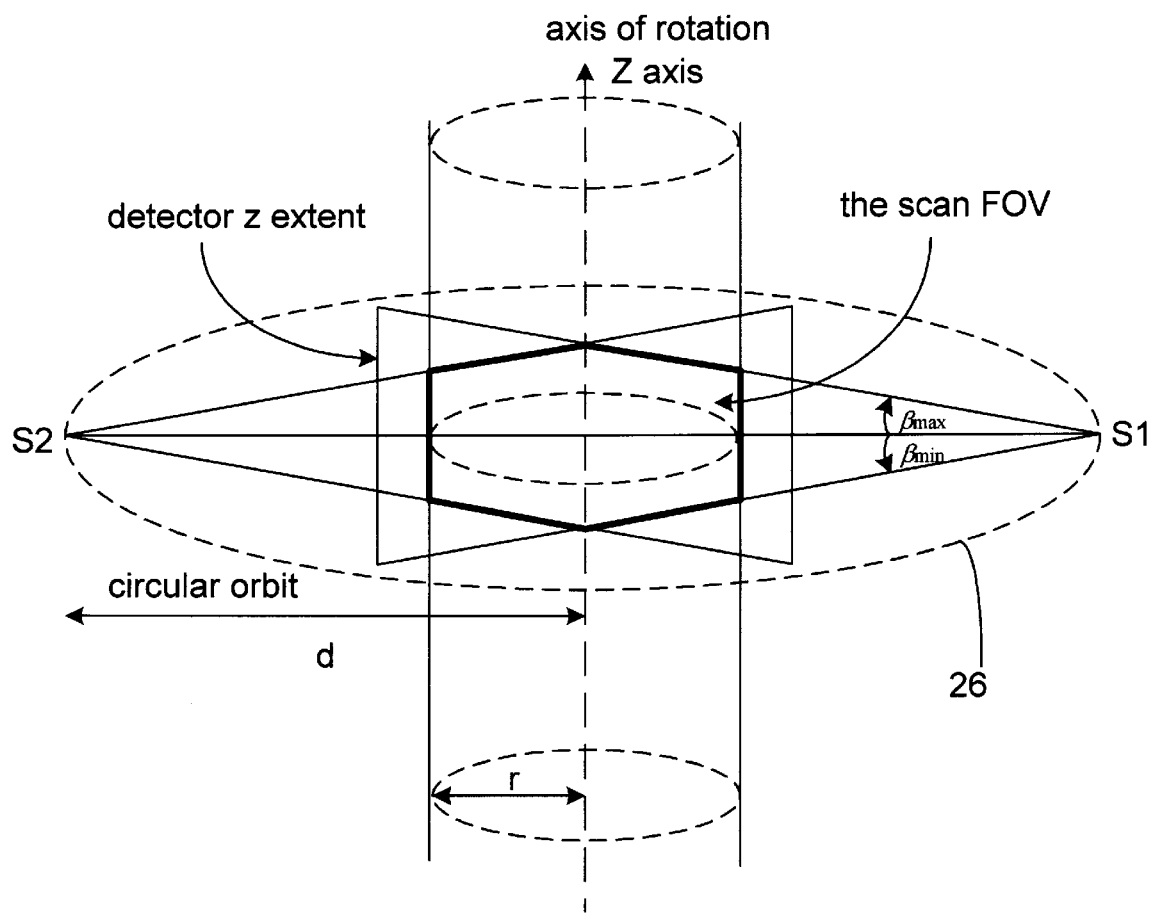
FIG. 6 is a schematic diagram illustrating an embodiment of the invention in connection with a longitudinally unbounded object.

FIG. 6 shows the geometry of the cone-beam CT scanner with limited detector z extent. The region within the heavy solid line in FIG. 6 indicates the cross-section of the measurable region for a given source location (S1). The measurable region is primarily determined by the detector extent and the imaging geometry. The scan field of view (FOV) is defined as the overlapping region of all measurable regions for all source locations in the circular scan. Thus, the scan FOV is defined by a cylinder ended with a cone on each end, whose axes coincide with the axis of rotation. The cross-section of the scan FOV is darkly shaded in FIG. 6. The radius of the cylinder is determined by the detector in-plane extent and the imaging geometry. The top and bottom cones are determined by the upper and lower cone angles, $\beta_{max}$ and $\beta_{min}$ shown in FIG. 6.

Missing some projection measurements due to the limited detector z extent will introduce errors. In general, these errors may propagate inwardly from the top and the bottom and contaminate the reconstruction in the top and bottom layers of the scan FOV. The depth of the contaminated layers, referred to as the contamination depth, are determined by the error propagating distance along the Z direction. Different operators employed by different reconstruction algorithms will result in different contamination depths.

The rod-like object raises a challenging problem for cone beam CT scan and reconstruction in general. However, this invention provides a solution to this problem.

The contamination depth for each term in Equation 1 was analyzed by examining the. 2, 3, and 4 or 5–7. It is concluded from Equation 2 that the first term, that is, the Feldkamp reconstruction has a zero contamination depth since no operation causes the errors to propagate in the Z direction. It is concluded from Equation 3 that the contamination depth of the second term is half of the detector Z cell pitch since a difference operator (Equation 3a) is applied in the Z direction. Furthermore, it is concluded from numerical analyses of Equation 5–7 that the contamination depth of the third term is one detector Z cell pitch.

Once the contamination depth for each term is quantified, the strategy for imaging the rod-like object becomes clear. Since the maximum depth of the contaminated layer for this hybrid algorithm is one detector Z cell pitch, these contaminated layers can be excluded by slightly modifying the definition of the scan FOV so that its cone ends move inwardly by one detector Z cell pitch at both ends.

Thus, for the primary-plus-supplementary scan path cone-beam CT using the reconstruction algorithms proposed in this invention, the reconstruction within the modified scan FOV does not require the missing measurements due to the limited detector z extent. Therefore, exact regional reconstruction of the longitudinally-unbounded object can be achieved within the modified scan FOV.

Furthermore, the longitudinally-unbounded (rod-like) object can be imaged section by section, where each section is imaged by one primary-plus-supplementary scan. To maximize the volume coverage speed of contiguous exams, the maximum longitudinal displacement between the adjacent primary scans is chosen so that within the object to be imaged no gap exists between the adjacent modified scan FOVs.

While FIG. 1 shows a planer detector array 16, it will be understood that another embodiment of the invention could employ a different type of detector, such as an array of detector cells lying along a curved surface, or even a single detector cell or linear array of detector cells acquiring the cone beam projection data sequentially.

Obviously, many other modifications and variations of the present invention are possible in light of the above teachings. It is therefore to be understood that within the scope of the disclosed concept, the invention may be practiced otherwise than as specifically described.

What is claimed is:

1. In an imaging system wherein a detector is mounted for measuring radiation emanating in a cone beam of rays which converge at a focal point, a method for reconstructing an image of an object comprising the steps of:

establishing relative movement between said cone beam focal point and said object along a composite scan path, comprising primary and supplementary scan path components;

acquiring a set of cone beam data of said object with said detector during movement along said supplementary scan path component, said cone beam data associated with said supplementary scan path to be used only for deriving information which cannot be derived from other cone beam data that is associated with the primary scan path;

computing a set of values of an intermediate function from said cone beam data, each of said computed values having an associated location defined by a prespecified point grid lying on the detector plane; and employing each of said computed values to compute the supplementary component of a reconstruction function of said object.

2. The method of claim 1 wherein said object comprises a longitudinally-unbounded object, and said method comprises the further steps of:

defining a scan field of view relative to said imaging system;

determining error propagation distance in the direction along the normal of a plane containing the primary scan path;

modifying the definition of the scan field of view, according to said error propagation distance; and generating the reconstruction within the modified field of view from the composite scan path.

3. The method of claim 2 wherein:

repeated supplementary scans are made at different selected locations along a Z-axis positioned with respect to said object until an entire longitudinal extent of the longitudinally-unbounded object is imaged.

4. The method of claim 2 wherein:

repeated primary scans are made at different selected locations along a Z-axis positioned with respect to said object until an entire region of interest of the object is imaged.

5. The method of claim 4 wherein:

the maximum longitudinal displacement between adjacent primary scans, along said Z-axis, is chosen so that within said object no gap exists between the modified fields of view of said adjacent primary scans.

6. The method of claim 1 wherein:

said supplementary scan path component comprises at least a linear component.

7. The method of claim 1 wherein:

said primary scan path component comprises at least a circular component.

8. The method of claim 1 wherein:

said value of said reconstruction function is computed by means of interpolation of values of said intermediate function.

9. The method of claim 1 wherein:

said step of computing the values of said intermediate function comprises summing weighted cone beam data only along the lines representing those planes not intersecting the primary scan path.

10. The method of claim 1 wherein:

said supplementary scan path component comprises at least a helical component.

11. In an imaging system wherein a detector is mounted for measuring radiation emanating in a cone beam of rays which converge at a focal point, a method for reconstructing an image of an object comprising the steps of:

establishing relative movement between said cone beam focal point and said object along a composite scan path, comprising primary and supplementary scan path components;

acquiring a set of cone beam data of said object with said detector during movement along said supplementary scan path component;

computing a set of values of an intermediate function from said cone beam data, each of said computed values having an associated location defined by a prespecified point grid lying on the detector plane, said values of said intermediate function being computed on the detector plane on a grid whose sampling spacing is substantially greater than that of the detector elements projected on the detector plane; and employing each of said computed values to compute the supplementary component of a reconstruction function of said object.

12. In an imaging system wherein a detector is mounted for measuring radiation emanating in a cone beam of rays which converse at a focal point, a method for reconstructing an image of an object comprising the steps of:

computing at least one part of the said reconstruction on a sparser three-dimensional image grid, which, compared with a full-size image grid, has a larger spacing between points in the x, y, and/or z directions;

combining thumbnail reconstructions of all said computed parts;

generating a combined full size reconstruction of said computed parts from the combined thumbnail reconstructions by interpolation; and combining the interpolated full size reconstruction with the full-size reconstructions of other parts to produce the complete full-size reconstruction.

13. In an imaging system wherein a detector is mounted for measuring radiation emanating in a cone beam of rays which converge at a focal point, a method for reconstructing an image of the object comprising the steps of:

establishing relative movement between said cone beam focal point and said object along a composite scan path comprising primary and curved supplementary components;

acquiring a set of cone beam data of said object with said detector during movement along said curved supplementary scan path; and deriving an intermediate function from said cone beam data for use in forming the supplementary component of the reconstruction function of said object.

14. The method of claim 13 wherein:

said method includes acquiring a second set of cone beam data of said object during movement along said primary scan path, generating a primary component reconstruction function from said second set of cone beam data, and combining said primary component reconstruction function with said supplementary component reconstruction function to provide an image of said object.

15. The method of claim 14 wherein said method includes the steps of:

computing at least one part of the said reconstruction on a sparser three-dimensional image grid, which, compared with a full-size image grid, has a larger spacing between points in the x, y, and/or z directions;

combining thumbnail reconstructions of all said computed parts;

generating a combined full size reconstruction of said computed parts from the combined thumbnail reconstructions by interpolation; and combining the interpolated full size reconstruction with the full-size reconstructions of other parts to produce the complete full-size reconstruction.

16. The method of claim 14 wherein:

said reconstruction method includes a filtering step applied to at least some parts of the said reconstruction in selected relation to the backprojection step.

17. The method of claim 14 wherein said object comprises a longitudinally-unbounded object, and said method comprises the further steps of:

defining a scan field of view relative to said imaging system;

determining error propagation distance in the direction along the normal of a plane containing the primary scan path modifying the definition of the scan field of view, according to said error propagation distance; and generating the reconstruction within the modified field of view from the composite scan path.

18. The method of claim 19 wherein:

the maximum longitudinal displacement between adjacent primary scans, along said Z-axis is chosen so that within said object no gap exists between the modified fields of view of said adjacent primary scans.

19. The method of claim 17 wherein:

repeated primary scans are made at different selected locations, along a Z-axis positioned with respect to said object until an entire region of interest of the object is imaged.

20. The method of claim 17 wherein:

repeated supplementary scans are made at different selected locations along a Z-axis positioned with respect to said object until an entire longitudinal extent of the longitudinally-unbounded object is imaged.

21. The method of claim 13 wherein:

said supplementary scan path component comprises at least a helical component.

22. The method of claim 13 wherein:

said primary scan path component comprises at least a circular component.

23. The method of claim 13 wherein:

said value of said reconstruction function is computed by means of interpolation of values of said intermediate function.

24. The method of claim 13 wherein:

the values of said intermediate function are computed on a detector plane on a grid whose sampling spacing is substantially greater than that of the detector elements projected on the detector plane.

25. The method of claim 13 wherein said deriving step comprises:

computing a set of values of an intermediate function from said cone beam data, each of said computed values having an associated location defined by a prespecified point grid lying on the detector plane; and employing each of said computed values to compute the supplementary component of reconstruction of said object.

26. The method of claim 13 wherein:

said cone beam data associated with movement along the supplementary scan path is used only for deriving information which cannot be derived from other cone beam data that is associated with the primary scan path.

27. The method of claim 13 wherein:

said step of computing the values of said intermediate function comprises summing weighted cone beam data only along the lines representing those planes not intersecting the primary scan path.

\* \* \* \* \*